(12) United States Patent
Hashaikeh et al.

(10) Patent No.: US 8,691,893 B2
(45) Date of Patent: Apr. 8, 2014

(54) BIODEGRADABLE COMPOSITE MATERIALS

(75) Inventors: Raed Hashaikeh, Abu Dhabi (AE);
Parakalan Krishnamachari, Abu Dhabi (AE)

(73) Assignee: Masdar Institute of Science and Technology, Abu Dhabi (AE)

( * ) Notice: Subject to any disclaimer, the term of this patent is extended or adjusted under 35 U.S.C. 154(b) by 166 days.

(21) Appl. No.: 13/268,278

(22) Filed: Oct. 7, 2011

(65) Prior Publication Data
US 2013/0090401 A1 Apr. 11, 2013

(51) Int. Cl.
C08G 18/38 (2006.01)
C08G 63/08 (2006.01)
C08L 1/00 (2006.01)

(52) U.S. Cl.
USPC ............................................. 524/35; 525/150

(58) Field of Classification Search
USPC ............................................. 524/35; 525/450
See application file for complete search history.

(56) References Cited

U.S. PATENT DOCUMENTS

| | | | |
|---|---|---|---|
| 5,714,230 A * | 2/1998 | Kameoka et al. | 428/141 |
| 5,763,098 A * | 6/1998 | Kameoka et al. | 428/481 |
| 6,103,790 A * | 8/2000 | Cavaille et al. | 524/13 |
| 7,256,223 B2 * | 8/2007 | Mohanty et al. | 523/124 |
| 7,265,188 B2 * | 9/2007 | Autran | 525/439 |
| 7,888,412 B2 * | 2/2011 | Holbrey et al. | 524/27 |
| 2002/0094444 A1 * | 7/2002 | Nakata et al. | 428/480 |
| 2008/0118765 A1 * | 5/2008 | Dorgan et al. | 428/532 |
| 2009/0298976 A1 * | 12/2009 | Yano et al. | 524/35 |
| 2010/0125112 A1 | 5/2010 | Chung et al. | |
| 2010/0144932 A1 | 6/2010 | Kwon et al. | |
| 2010/0222460 A1 * | 9/2010 | Hojo | 524/35 |
| 2010/0233468 A1 * | 9/2010 | Ioelovich et al. | 428/326 |
| 2010/0240806 A1 * | 9/2010 | Kondo | 524/35 |
| 2011/0130488 A1 * | 6/2011 | Yoshino et al. | 524/35 |
| 2011/0144241 A1 * | 6/2011 | Yoshino et al. | 524/35 |
| 2011/0196094 A1 * | 8/2011 | Hamad et al. | 525/54.21 |
| 2011/0282049 A1 * | 11/2011 | Shelton et al. | 536/58 |
| 2012/0010334 A1 * | 1/2012 | D'Andola et al. | 524/35 |
| 2012/0283363 A1 * | 11/2012 | Kumamoto et al. | 524/35 |

OTHER PUBLICATIONS

Petersson et al. (Composites Science and Technology 67 2007 2535-2544).*

Petersson et al. Composites Science and Technology 67 2007 2535-2544.*

* cited by examiner

*Primary Examiner* — Liam Heincer
(74) *Attorney, Agent, or Firm* — Myers Bigel Sibley & Sajovec, P.A.

(57) ABSTRACT

A method of making a biodegradable composite is carried out by: (a) providing an aqueous mixture comprising partially hydrolyzed cellulose in a dissolution media; (b) providing a solution comprising a aliphatic polyester in a polar organic solvent; (c) combining the mixture with the solution to form a precipitate; (d) washing the precipitate with water to remove solvent and dissolution media and form a wet biodegradable composite; and then (e) drying the wet biodegradable composite to form a dry biodegradable composite. Composites made from the method are also described.

15 Claims, 8 Drawing Sheets

Image of the PLA cellulose nanocomposite material

Figure 1: Image of the PLA cellulose nanocomposite material

Figure 2: Schematic representation of NCC extraction using hydrolysis

Figure 3: DMA—Storage modulus as a function of temperature for neat PLA and PLA nanocomposites at various loading levels of NCC Figure 4: Tan theta curves of neat PLA and PLA nanocomposites.

Figure 5: DSC thermographs of neat PLA and PLA nanocomposites

Figure 6: TGA thermographs for neat PLA and PLA nanocomposites.

Figure 7: Derivative weight loss from TGA for Neat PLA and PLA nanocomposite

Figure 8: SEM images of PLA nanocomposite material. NCC30 (left) and NCC50 (right)

Figure 9: X-ray diffraction pattern of neat PLA and PLA nanocomposite

_US 8,691,893 B2_

BIODEGRADABLE COMPOSITE MATERIALS

FIELD OF THE INVENTION

The present invention concerns biodegradable composite materials and methods of making the same.

BACKGROUND OF THE INVENTION

Convenience, safety, low price and good aesthetic qualities are among the major factors that makes plastics useful for numerous applications. Synthetic polymers that are produced from petrochemical products have low recovery/reproduction rates and are not easily degraded in the environment.

New bio-based materials have been explored to develop edible and biodegradable films to tackle the issue of polymeric waste materials (Tharanathan, 2003). Among various biodegradable polymers, poly (lactic acid) (PLA), biodegradable aliphatic polyester is an ideal candidate due to the fact that it can be derived from 100% renewable resources, such as corn and sugar beets. PLA is widely used in medical applications and has a great potential in the packaging industry (Bastioli, 2001; Lunt, 1998).

While biodegradable polymers are environmentally benign and are often produced from sustainable agricultural raw materials, the penetration of biodegradable polymers in the marketplace has encountered various barriers including cost and performance issues. For example, some of the properties such as brittleness, low heat distortion temperature, high gas permeability, and low melt viscosity for further processing restrict their use in a wide range of applications (Sinha Ray, Yamada, Okamoto, Fujimoto, Ogami & Ueda, 2003). Modification of the biodegradable polymers through innovative nanotechnology opens up new possibilities for improving not only the properties but also the cost-price-efficiency.

SUMMARY OF THE INVENTION

A first aspect of the invention is a method of making a biodegradable composite, comprising:

(a) providing an aqueous mixture comprising partially hydrolyzed cellulose in a dissolution media;

(b) providing a solution comprising a aliphatic polyester in a polar organic solvent;

(c) combining the mixture with the solution to form a precipitate; and then (d) washing the precipitate with water to remove solvent and dissolution media and form a wet biodegradable composite; and then (e) drying the wet biodegradable composite to form a dry biodegradable composite.

In some embodiments, the combining step, and the washing step, is carried out in a form or mold; and the method further comprises the step of: (e) releasing the biodegradable composite from the form or mold to produce a biodegradable composite article (optionally having a shape corresponding to the shape of the form or mold), and then optionally (f) cutting or grinding the article to further define the features thereof A second aspect of the invention is a shaped article produced by the process described herein.

A further aspect of the invention is a particulate biodegradable composite produced by the process described herein.

The foregoing and other objects and aspects of the present invention are explained in greater detail in the drawings herein and the specification set forth below. The disclosures of all United States Patent references cited herein are to be incorporated by reference herein in their entirety.

DETAILED DESCRIPTION OF THE PREFERRED EMBODIMENTS

"Cellulose" as used herein may comprise, consist of or consist essentially of any suitable natural cellulose material or partially processed cellulose, including but not limited to microcrystalline cellulose, hydroxymethyl cellulose, cellulose per se (e.g., cotton cellulose), hydroxypropyl cellulose, methylcellulose, and combinations thereof.

"Microcrystalline cellulose" is known. It is typically a purified, partially depolymerized cellulose that is prepared by treating alpha cellulose, in the form of a pulp manufactured from fibrous plant material, with mineral acids. See, e.g., U.S. Pat. No. 4,744,987. It is a generally white, odorless, tasteless, relatively free flowing powder that is generally insoluble in water, organic solvents, dilute alkalis and dilute acids. U.S. Pat. Nos. 2,978,446 to Battista et al. and 3,146,168 to Battista describe microcrystalline cellulose and its manufacture; the latter patent concerns microcrystalline cellulose for pharmaceutical applications.

"Dissolution media" as used herein may be any suitable dissolution media. In general, such a media breaks or disrupts the hydrogen bonding between individual cellulose chains and substantially isolates individual cellulose chains by surrounding them with ions and solvent molecules. Examples of dissolution media include, but are not limited to, acid solutions such as sulfuric acid, nitric acid, phosphoric acid, organic solvents, ionic liquids, basic solutions (e.g., NaOH, NaOH/Urea solutions) LiCl/DMAc solutions, and the like, including suitable combinations thereof.

"Aliphatic polyester" as used herein may be any suitable aliphatic polyester, including but not limited to polylactic acid, polyglycolic acid, polycaprolactone, polybutylene succinates, polyhydroxyalkanoates, and combinations thereof. Additional examples include, but are not limited to, those described in U.S. Pat. Nos. 8,008,373; 8,003,721; 8,003,719; and 7,994,078, the disclosures of which are incorporated by reference herein in their entirety.

As noted above, the present invention provides a method of making a biodegradable composite, comprising:

(a) providing an aqueous mixture comprising partially hydrolyzed cellulose in a dissolution media;

(b) providing a solution comprising a aliphatic polyester in a polar organic solvent;

(c) combining the mixture with the solution to form a precipitate; and then (d) washing the precipitate with water to remove solvent and dissolution media and produce a wet biodegradable composite; and then (e) drying the wet biodegradable composite to produce a dry biodegradable composite.

The washing step may be carried out continuously or as a batch process by any suitable technique, such as by mixing and separating (e.g., by settling, filtration, or centrifugation), washing of a "cake", dialysis, and combinations thereof. Washing may be carried out with distilled water, or the water may contain additional ingredients such as salts, buffers, etc. Specific washing steps may be repeated and/or continued until the desired degree of washing is achieved. In some embodiments, the washing step is carried out until the wet biodegradable composite has a neutral pH (e.g., a pH between 6 and 7).

The drying step may be carried out by any suitable means. In some embodiments, the drying step is carried out at room temperature, with heating (e.g., baking), or during cooling (e.g., chilling or freezing). The drying step can be carried out at any suitable pressure, including atmospheric pressure or at a reduced pressure (e.g., as in freeze drying).

The dry biodegradable composite so produced is preferably rigid. In some embodiments, the biodegradable composite so produced has (i) a storage modulus represented by an integer between 1 or 5 gigapascals, up to 20, 25, or 35 gigapascals, at a temperature of 20 degrees C., and/or (ii) a storage modulus represented by an integer between 0.1 or 1 gigapascals, up to 10 or 20 gigapascals, at a temperature of 100 degrees Centigrade.

In some embodiments, the dry biodegradable composite so produced is porous.

In some embodiments, the dry biodegradable composite so produced has a density of 0.01, 0.05 or 0.1 grams per cubic centimeter, up to 0.5, 1, 5 or 10 grams per cubic centimeter.

In some embodiments, the biodegradable composite has a residual weight of about 1, 2 or 5 percent to 10, 15, or 20 percent at a temperature of 400 degrees C.

If desired, the combining step, and the optional washing and/or dialyzing step, can be carried out in a form or mold. In this case the method can further comprises the step of: (e) releasing the biodegradable composite from the form or mold to produce a biodegradable composite article (optionally having a shape corresponding to the shape of the form or mold), optionally followed by the steps of: (f) cutting or grinding the article to further define the features thereof, and/or (g) grinding the article to form a particulate biodegradable composite.

Thus the method of the invention can be used for the purpose of producing an insulating article, as may be used for architectural or building purposes, or configured for refrigeration, chilling and/or freezing apparatus. In addition, articles of the invention may be configured for use as a tissue engineering scaffold, as may be used for bone or soft tissue regeneration in vitro or in vivo, Particulate biodegradable composites produced by the methods of the present invention are useful as, among other things, a pharmaceutical tablet filler or excipient.

The present invention is explained in greater detail in the following non-limiting Examples.

EXAMPLE 1

Acid hydrolysis of cellulose is a popular method for isolating nanocrystalline cellulose (NCC) from cellulose fibers. Since the first publication related to the extraction (Mukherjee & Woods, 1953; Revol, Godbout, Dong, Gray, Chanzy & Maret, 1994; Revol, Bradford, Giasson, Marchessault & Gray, 1992) and use of NCC as reinforcing fillers based nanocomposites (Favier, Chanzy & Cavaille, 1995), they have attracted a great deal of interest in the nanocomposites field (Noishiki, Nishiyama, Wada, Kuga & Magoshi, 2002; Qi, Cai, Zhang & Kuga, 2009; Roman & Winter William, 2006) due to their appealing intrinsic properties such as nanoscale dimensions, high surface area, unique morphology, low density, and mechanical strength.

Cellulose nanocomposites have been prepared using solution casting (Favier, Chanzy & Cavaille, 1995), In situ polymerization (Wu Q, 2002) and melt intercalation (Chazeau, Cavaillé, Canova, Dendievel & Boutherin, 1999).

The research in this study represents our most recent and novel effort of preparing biodegradable composites of PLA and cellulose using solvents mixing method.

Materials.

PLA under the commercial name PLA 4060D (poly-D/L-lactide or PDLLA) was provided in the form of pellets. PLA 4060D has about 11 to 13% D-lactide content and has a density of 1.24 g/c.c. It has an amorphous morphology and melting temperature in the range of 150-180 C. Microcrystalline cellulose (MCC) was provided by FMC Bio Polymer (Avicel-PH101). Sulfuric acid, 95-97%, Reagent Grade, was purchased from Scharlau. Tetrahydrofuran (THF) solvent was purchased from Sigma-Aldrich.

Processing.

PLA was dissolved in a solvent such as THF. At the same time, Microcrystalline cellulose (MCC) was hydrolyzed in a different container via hydrolyzing with 64%, 65% or 66% $H_2SO_4$ at ambient for 30, 60, 120 or 180 minutes. A ratio of 1 g:10 ml was adopted for the hydrolysis reactions (MCC: $H_2SO_4$). The two mixtures were then mixed with constant stirring. Upon mixing and washing, a white material is precipitated.

The product is collected and washed with DI water through centrifugation and dialysis. The samples were dried and stored. Using this procedure 4 samples were produced at loading levels of 1%, 5%, 10%, 15%, 30% and 50% (w/w) of MCC (the weight percentages are taken with reference to the starting material MCC).

Characterization.

DMA:

The dried nanocomposite samples were ground in a variable speed mill, using a 1 mm Sieve. The fine powder was used for the DMA experiment. The powder was contained in metal pockets (Perkin Elmer part no: N533-0322) and the DMA was run in the single cantilever mode from 25° C. to 240° C. at a ramp rate of 2° C./min at a constant frequency of 1 Hz. This is a comparative test; different tests will give different numbers of the storage modulus of the same material.

TGA and DSC:

Thermogravimetric analyzer (TGA): Thermogravimetric analyses of the various samples (about 10-15 mg) were done with Perkin Elmer (TGA 4000) with a heating rate of 10° C./min up to 800° C. in nitrogen environment. Differential scanning calorimeter (DSC): The sample, 6-10 mg, was analyzed 87 by increasing the temperature at a rate of 2° C./min in nitrogen environment.

SEM:

The morphology of the nanocomposite was characterized using a FEI SEM under high vacuum mode and low acceleration voltage. The samples were sputter coated with Au or Carbon.

XRD:

X-ray diffractograms of the neat polymer and the nanocomposite material were obtained on an X-ray diffractometer (PANalytical, X'PertPro). The scan was conducted for duration of 30 minutes for the scan range of 7-70° 2θ.

Figure 1:
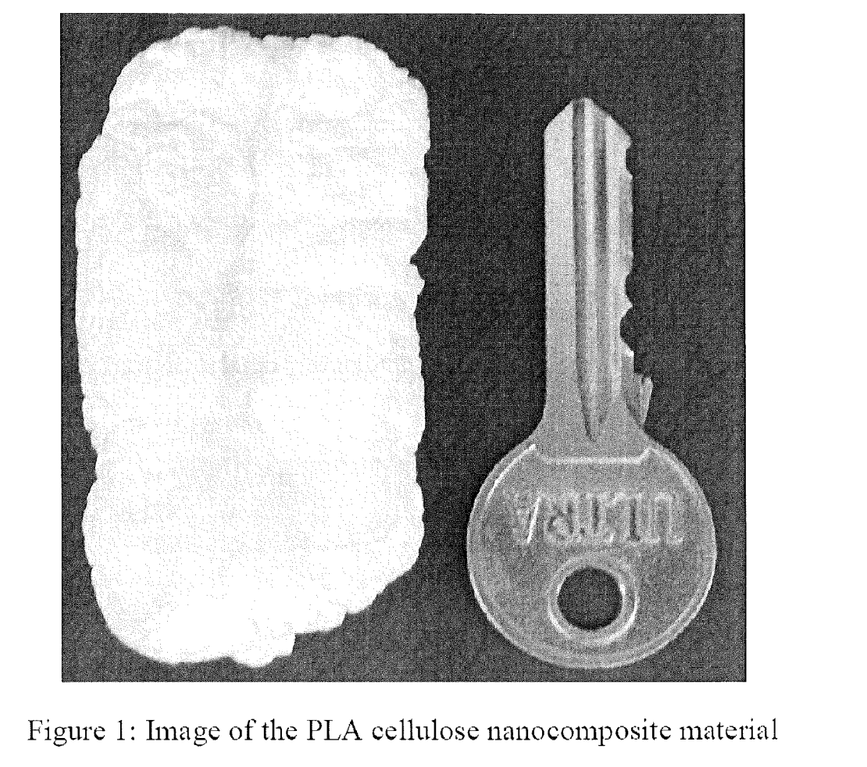
FIG. 1: Image of PLA cellulose composite material.
Figure 2:
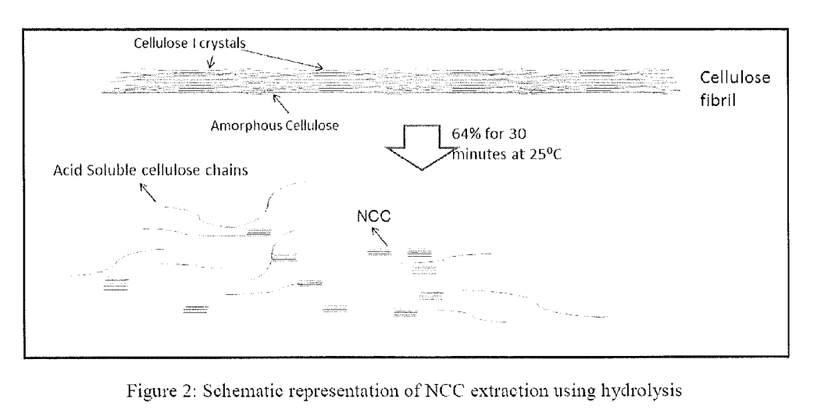
FIG. 2: Schematic representation of composite extraction using hydrolysis.

Results and Discussion:

The composite material forms immediately upon mixing. The resulting material is white, hard and different from MCC and PLA in physical appearance (FIG. 1). The conditions used to prepare the acid/cellulose mixture, where chosen to open the cellulose structure and free nanocrystalline cellulose (NCC) whiskers and at the same time minimize hydrolysis of amorphous cellulose. Sulfuric acid concentration was 64% which is the concentration reported (Revol, Godbout, Dong, Gray, Chanzy & Maret, 1994; Revol, Bradford, Giasson, Marchessault & Gray, 1992) to open the cellulose structure and at which NCC is extracted. After 30 minutes in 64% sulfuric acid, we believe that cellulose amorphous part is dissolved and separated from NCC (FIG. 2). PLA is soluble in THF and amorphous cellulose is soluble in sulfuric acid with the NCC dispersed. At the same time, upon mixing, the THF acts as anti-solvent for dissolved cellulose. Dissolved cellulose which exists together with the partially hydrolyzed cellulose can be precipitated (regenerated) with the addition of an excess of a polar solvent (anti-solvent) like THF (for more information on dissolved cellulose precipitation, we refer the reader to the following article (Hashaikeh R and Abushammala H. Acid mediated networked cellulose: Preparation and characterization. Carbohydrate Polymers (2010))). PLA precipitates as well in the process. The co-precipitating cellulose seems to enhance bonding between the NCC and the PLA matrix.

Figure 3:
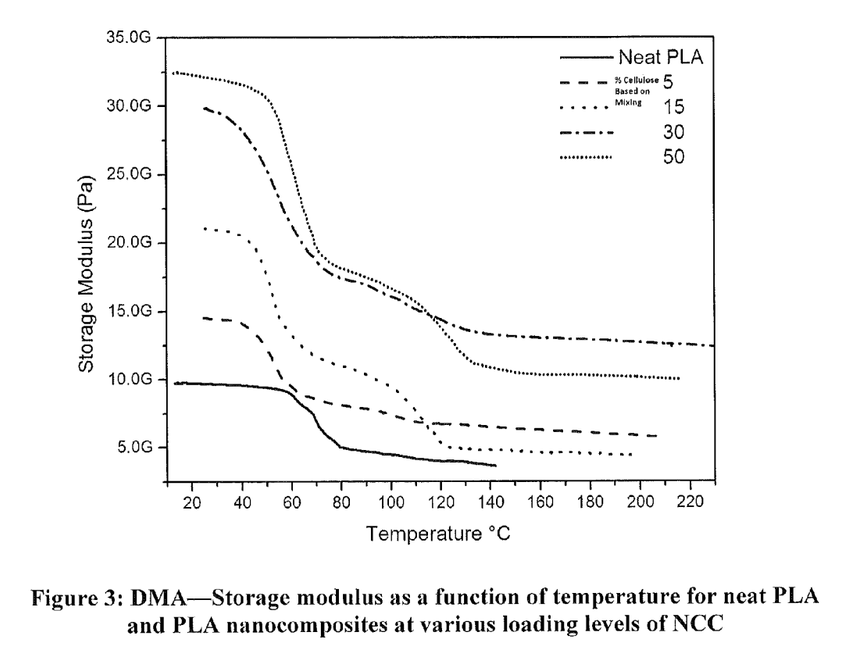
FIG. 3: DMA-Storage modulus as a function of temperature for neat PLA and PLA nanocomposites at various loading levels of composites.

DMA, TGA and DSC:

FIG. 3 shows Dynamic Mechanical Analysis (DMA) data of the PLA nanocomposite material with various loading levels of MCC, compared with neat PLA. It can be seen that the storage modulus (E') of all the blends are significantly improved over a wide range of temperature compared to that of the neat PLA. The storage modulus improvement is a function of cellulose content and is highest for sample NCC50 at 32.5 GPa. The improvement for all the nanocomposites was most obvious below the glass transition temperature of PLA (50° C. to 60° C.). The modulus curve shows a drop for all the samples around the glass transition temperature and flattens out at a much lower temperature for the neat PLA (at 80° C.), whereas for the nanocomposites they flatten out at around 130 to 140° C.).

The steady increase in the storage modulus of the composite, with MCC content is indicative of the fact that efficient dispersion and blending of cellulose in the PLA matrix was possible even at high loading levels.

Figure 4:
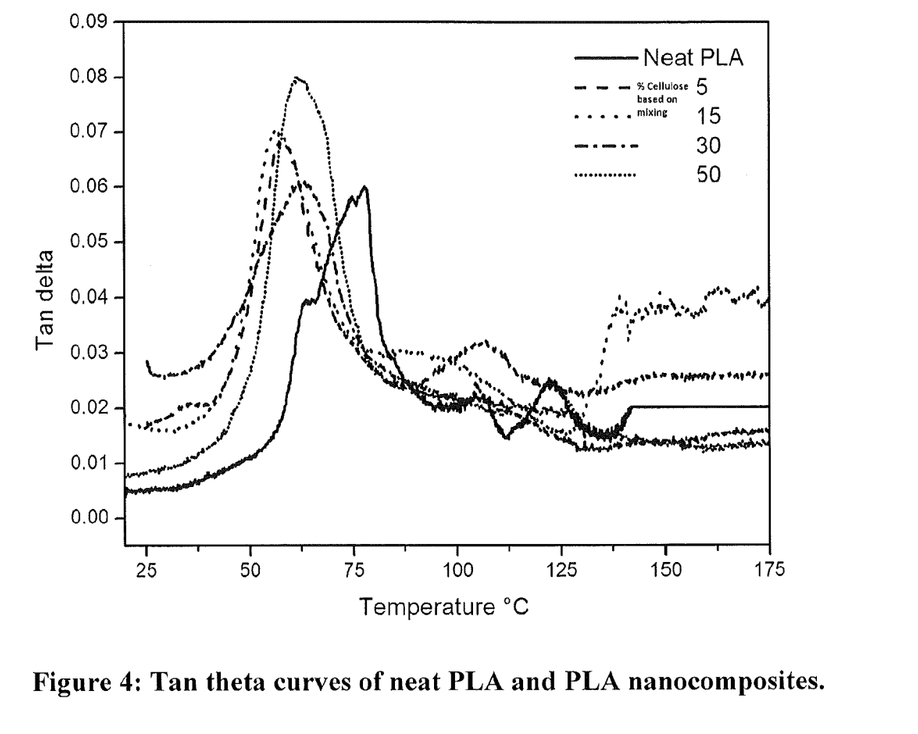
FIG. 4: Tan theta curves of Neat PLA and PLA nanocomposites.

Tan δ, also called damping, is a dimensionless property and is the ratio of loss to storage modulus. Tan δ curves for the various samples are shown in FIG. 4, It can be seen that the Tan δ peaks of the nanocomposites increased in 130 magnitude (highest for NCC50) and shifted towards a lower temperature as compared to the neat PLA. Mathew et al (Mathew Aji, Chakraborty, Oksman & Sain, 2006) also noticed this behavior of increase in magnitude of Tan δ peaks in their work with PLA nanocomposites through extrusion method.

Figure 5:
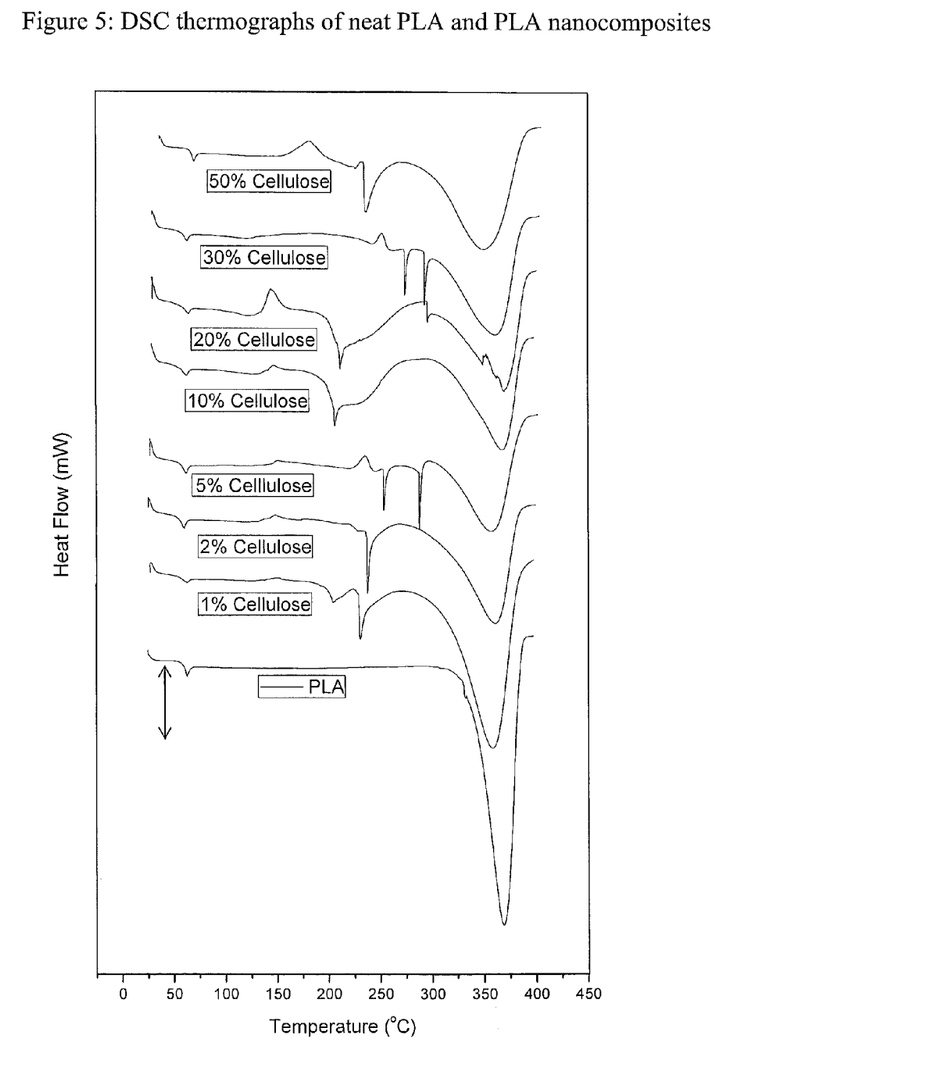
FIG. 5: DSC thermograms of Neat PLA and PLA nanocomposites.

FIG. 5 shows the DSC thermograms of various samples. It can be observed that the Tg of the nanocomposites are slightly shifted towards a lower temperature as compared to the neat PLA. This is in agreement with the Tan δ peaks shifting towards a slightly lower temperature as compared to the neat PLA.

Also evident from the thermograms is the introduction of the crystallinity into the otherwise almost completely amorphous PLA, indicated by the exothermic activity in the DSC traces for the nanocomposite.

Figure 6:
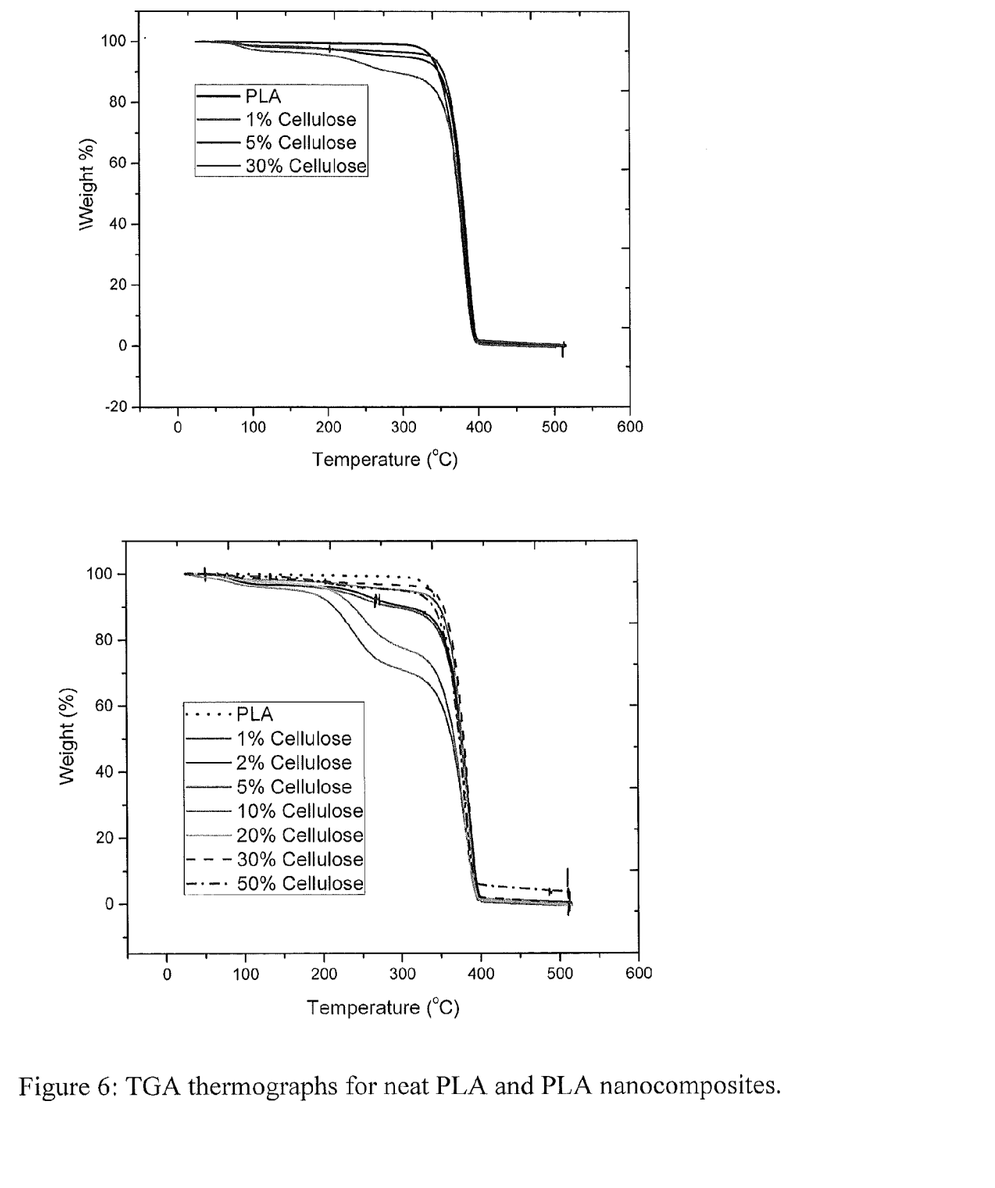
FIG. 6: TGA thermograms for Neat PLA and the PLA nanocomposites.

TGA data (FIG. 6) reveals that all the nanocomposites have the onset of thermal degradation at a much lower temperature than neat PLA. However the nanocomposites are seen to be more resilient and have a residual weight of about 5% at 400° C. at which point the PLA has lost all its weight. The nanocomposites eventually completely lose their weight at around 750° C.

Nanocrystalline cellulose particles have a greater number of free end chains due to their smaller particle size, introduced as a result of the hydrolysis treatment. The end chains start decomposing at lower temperature (Staggs, 2006), consequently, causing an increase of the char yield of these hydrolyzed samples (Piskorz, Radlein, Scott & Czernik, 1989). Also sulfate groups, introduced during hydrolysis with sulfuric acid could possibly be acting as a flame retardant (Roman & Winter, 2004).

Figure 7:
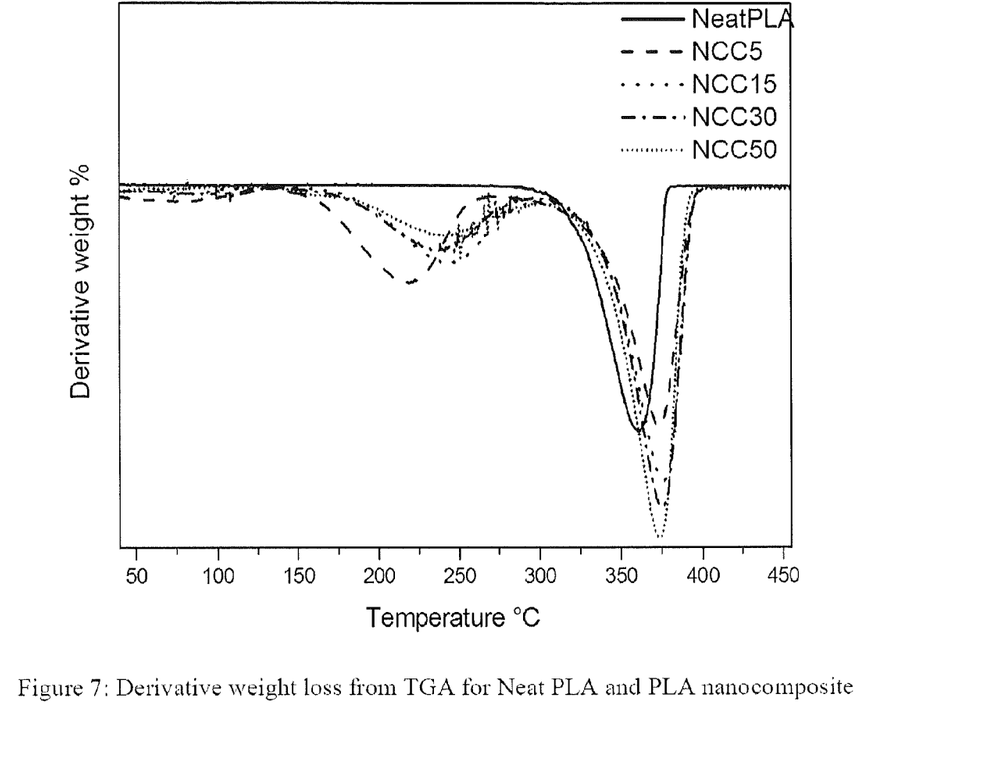
FIG. 7: Derivative weight loss from TGA for Neat PLA and PLA nanocomposites.

It is observed from the d-TGA curves (derivative weight loss curves) from FIG. 7, that there is a shift towards the positive direction in terms of the temperature at which maximum weight loss occurs. Important values from the TGA and d-TGA curves are listed in Table 1.

TABLE 1

TGA data for the PLA nanocomposites

| Sample | Onset of thermal degradation (TGA) ° C. | Temp at which max weight loss occurs (DTGA) ° C. |
|---|---|---|
| Neat PLA | 300 | 360 |
| NCC5 | 168 | 373 |
| NCC15 | 184 | 375 |
| NCC30 | 185 | 375 |
| NCC50 | 188 | 374 |

Figure 8:
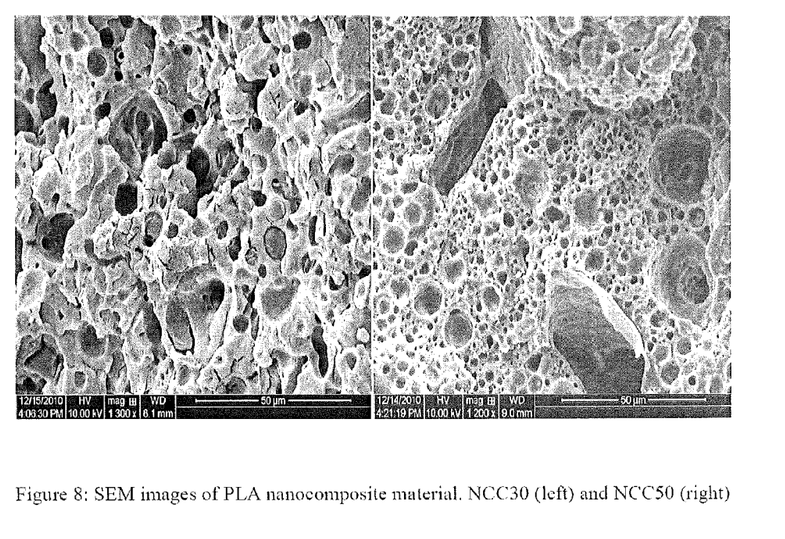
FIG. 8: SEM images of PLA nanocomposite materials. NCC30 (left) and NCC50 (right).

SEM and XRD:

FIG. 8 shows the SEM images of the nanocomposites. It was not possible to view the dispersion of the nanocellulose in the polymer matrix; however, interestingly enough it was observed that there was micro/nanoporosity introduced in the polymer matrix. This could have been made possible by the solvent escaping/leaching through the matrix during the drying process. Micro/nanoporosity is an important attribute for a potential bio medical application in tissue engineering and scaffolds (Lee et al., 2005; Paul & Robeson, 2008; Traversa et al., 2008). The presence of micro and nanopores could serve as potential active site for cell growth, blood vessel invasion, nutrient and metabolic waste transport. It is worth mentioning here that NCC50 exhibited more pores and variations than NCC30.

Figure 9:
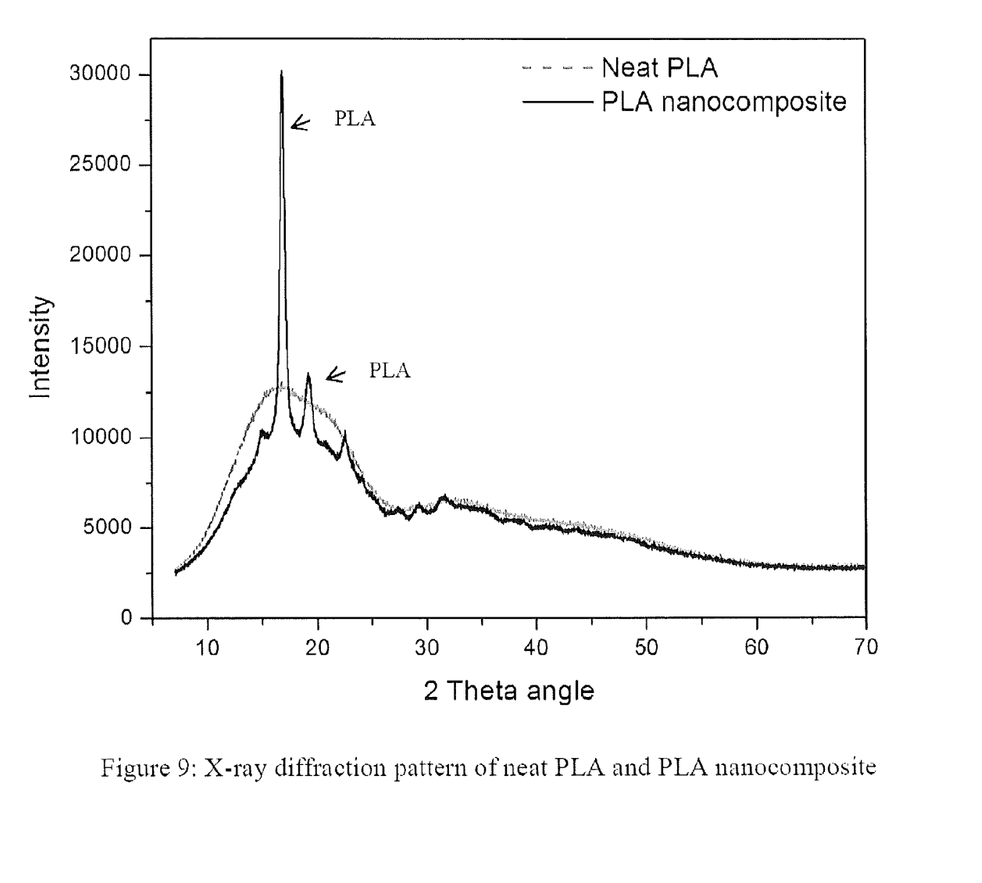
FIG. 9: X-ray diffraction pattern of neat PLA and PLA nanocomposite.

Diffraction patterns of Neat PLA and the nanocomposite material (NCC50) are shown in FIG. 9. The predominantly amorphous PLA is characterized by a broad peak. The nanocomposite is having sharp and intense peaks that are characteristic of crystalline PLA. Thus, the dissolved PLA in THF upon precipitation tends to be more ordered. 173 This can indicate that PLA precipitates in a slower rate than cellulose and it is possible that cellulose provide the backbone for PLA solidification.

CONCLUSION

Biodegradable polymer blends of poly (lactic acid) (PLA) and cellulose were prepared using a novel solvent mixing method, yielding significant improvement in the mechanical and thermal stability of the generated material. The co-precipitating cellulose during the composite processing method seems to have enhanced the bonding between the cellulose and PLA matrix. The storage modulus of the nanocomposites increased as a function of the cellulose content, indicating good dispersion of cellulose during processing. The nanocomposites had porous morphology and enhanced crystallinity. The tunable nature of the nanocomposite, prepared using this method, makes it a suitable candidate for packaging industry as well as tissue engineering purposes.

REFERENCES

Bastioli, C. (2001). Global Status of the Production of Bio-based Packaging Materials. Starch-Stärke, 189 53(8), 351-355.

Chazeau, L., Cavaillé, J. Y., Canova, G., Dendievel, R., & Boutherin, B. (1999). Viscoelastic properties of plasticized PVC reinforced with cellulose whiskers. *Journal of Applied Polymer Science*, 71(11), 1797-1808.

Favier, V., Chanzy, H., & Cavaille, J. Y. (1995). *Macromolecules*, 28, 6365.

Hashaikeh R and Abushammala H. Acid mediated networked cellulose:194 Preparation and characterization. Carbohydrate Polymers (2010), d. j. c.

Lee, Y. H., Lee, J. H., An, I.-G., Kim, C., Lee, D. S., Lee, Y. K., & Nam, J.-D. (2005). Electrospun dual-porosity structure and biodegradation morphology of Montmorillonite reinforced PLLA nanocomposite scaffolds. *Biomatenials*, 26(16), 3165-3172.

Lunt, J. (1998). Large-scale production, properties and commercial applications of polylactic acid polymers. *Polymer Degradation and Stability*, 59 (1-3), 145-152.

Mathew Aji, P., Chakraborty, A., Oksman, K., & Sain, M. (2006). The Structure and Mechanical Properties of Cellulose Nanocomposites Prepared by Twin Screw Extrusion. *Cellulose Nanocomposites* (Vol. 938, pp, 114-131): American Chemical Society.

Mukherjee, S. M., & Woods, H. J. (1953). X-ray and electron microscope studies of the degradation of cellulose by sulphuric acid. *Biochimica et Biophysica Acta*, 10, 499-511.

Noishiki, Y., Nishiyama, Y., Wada, M., Kuga, S., & Magoshi, J. (2002). Mechanical properties of silk fibroin-microcrystalline cellulose composite films. *Journal of Applied Polymer Science*, 86(13), 3425-3429.

Paul, D. R., & Robeson, L. M. (2008). Polymer nanotechnology: Nanocomposites. *Polymer*, 49(15), 187-3204.

Piskorz, J., Radlein, D. S. A. G., Scott, D. S., & Czernik, S. (1989). Pretreatment of wood and cellulose for production of sugars by fast pyrolysis. *Journal of Analytical and Applied Pyrolysis*, 16(2), 127-142.

Qi, H., Cai, J., Zhang, L., & Kuga, S. (2009). Properties of Films Composed of Cellulose Nanowhiskers and a Cellulose Matrix Regenerated from Alkali/Urea Solution. *Biomacromolecules*, 10(6), 1597-1602.

Revol, J.-F. o., Godbout, L., Dong, X.-M., Gray, D, G., Chanzy, H., & Maret, G. (1994). Chiral nematic suspensions of cellulose crystallites; phase separation and magnetic field orientation. *Liquid Crystals*, 16(1), 127-134.11 Revol, J. F., Bradford, H., Giasson, J., Marchessault, R. H., & Gray, D. G. (218 1992). Helicoidal self-ordering of cellulose microfibrils in aqueous suspension. *International Journal of Biological Macromolecules*, 14(3), 170-172.

Roman, M., & Winter William, T. (2006). Cellulose Nanocrystals for Thermoplastic Reinforcement: Effect of Filler Surface Chemistry on Composite Properties. *Cellulose Nanocomposites* (Vol. 938, pp. 99-113): American Chemical Society.

Roman, M., & Winter, W. T. (2004). Effect of Sulfate Groups from Sulfuric Acid Hydrolysis on the Thermal Degradation Behavior of Bacterial Cellulose. *Biomacromolecules*, 5(5), 1671-1677.

Sinha Ray, S., Yamada, K., Okamoto, M., Fujimoto, Y., Ogami, A., & Ueda, K. (2003). New polylactide/layered silicate nanocomposites. 5. Designing of materials with desired properties. *Polymer*, 44(21), 6633-6646.

Staggs, J. E. J. (2006). Discrete bond-weighted random scission of linear polymers. *Polymer*, 47(3), 897-906.

Tharanathan, R. N. (2003). Biodegradable films and composite coatings: past, present and future. *Trends in Food Science & Technology*, 14(3), 71-78.

Traversa, E., Mecheri, B., Mandoli, C., Soliman, S., Rinaldi, A., Licoccia, S., Forte, G., Pagliari, F., Pagliari, S., Carotenuto, F., Minieri, M., & Di Nardo, P. (2008). Tuning hierarchical architecture of 3D polymeric scaffolds for cardiac tissue engineering. *Journal of Experimental Nanoscience*, 3(2), 97-110.

Wu Q, L. X., Berglund L A. (2002). In: 23rd Risø international symposium on materials science, sustainable natural and polymeric composites-science and technology.

The foregoing is illustrative of the present invention, and is not to be construed as limiting thereof. The invention is defined by the following claims, with equivalents of the claims to be included therein.

That which is claimed is:

1. A method of making a biodegradable composite, comprising:
   (a) providing an aqueous mixture comprising partially hydrolyzed cellulose in a dissolution media;
   (b) providing a solution comprising a aliphatic polyester in a polar organic solvent;
   (c) combining said mixture with said solution to form a precipitate; and then
   (d) washing said precipitate with water to remove solvent and dissolution media and form a wet biodegradable composite; and then
   (e) drying said wet biodegradable composite to produce a dry biodegradable composite.

2. The method of claim 1, wherein said biodegradable composite is rigid.

3. The method of claim 1, wherein said biodegradable composite is porous.

4. The method of claim 1, wherein said biodegradable composite has a density of 0.05 to 1 grams per cubic centimeter.

5. The method of claim 1, wherein said washing step is carried out until said wet biodegradable composite has a neutral pH.

6. The method of claim 1, wherein said drying step is carried out at room temperature, with heating, or during cooling, and wherein said drying step is carried out at atmospheric pressure or at a reduced pressure.

7. The method of claim 1, wherein said aliphatic polyester is selected from the group consisting of polylactic acid, polyglycolic acid, polycaprolactone, polybutylene succinates, polyhydroxyalkanoates, and combinations thereof.

8. The method of claim 1, wherein said polar organic solvent comprises tetrahydrofuran, chloroform, or combinations thereof.

9. The method of claim 1, wherein said dissolution media comprises an acid solution.

10. The method of claim 1, wherein:
said aliphatic polyester is selected from the group consisting of polylactic acid, polyglycolic acid, polycaprolactone, polybutylene succinates, polyhydroxyalkanoates, and combinations thereof;
said polar organic solvent comprises tetrahydrofuran, chloroform, or combinations thereof; and
said dissolution media comprises a sulfuric acid solution; and wherein said dry biodegradable composite has:
(i) a storage modulus of from 1 to 25 gigapascals at a temperature of 20 degrees C.;
(ii) a storage modulus of from 1 to 10 gigapascals at a temperature of 100 degrees Centigrade; and
(iii) a density of 0.1 to 0.5 grams per cubic centimeter.

11. The method of claim 1, wherein said combining step and said washing step are carried out in a form or mold; and said method further comprises the step of:
(e) releasing said biodegradable composite from said form or mold before or after said drying step to produce a biodegradable composite article.

12. The method of claim 11, further comprising the step of:
(f) cutting or grinding said article to further define the features thereof.

13. The method of claim 11, further comprising the step of:
(g) grinding said article to form a particulate biodegradable composite.

14. A particulate biodegradable composite produced by the process of claim 13.

15. The particulate biodegradable composite of claim 14, wherein said particulate is a pharmaceutical tablet filler.

* * * * *

UNITED STATES PATENT AND TRADEMARK OFFICE
CERTIFICATE OF CORRECTION

Page 1 of 1

PATENT NO. : 8,691,893 B2
APPLICATION NO. : 13/268278
DATED : April 8, 2014
INVENTOR(S) : Hashaikeh et al.

It is certified that error appears in the above-identified patent and that said Letters Patent is hereby corrected as shown below:

In the Claims:
Column 8, Claim 1, Line 35:
    After "dissolution media" in line 35, please add -- wherein said dissolution media comprises an acid solution, and ionic solution, or a basic solution; --

Signed and Sealed this
Seventeenth Day of March, 2015

Michelle K. Lee
*Director of the United States Patent and Trademark Office*